United States Patent
Gruber et al.

(10) Patent No.: US 10,825,547 B2
(45) Date of Patent: Nov. 3, 2020

(54) DETERMINING NOVEL ENZYMATIC FUNCTIONALITIES USING THREE-DIMENSIONAL POINT CLOUDS REPRESENTING PHYSICO CHEMICAL PROPERTIES OF PROTEIN CAVITIES

(71) Applicant: Innophore GmbH, Graz (AT)

(72) Inventors: Karl Gruber, Graz (AT); Georg Steinkellner, Kainach (AT); Christian Gruber, Weiz (AT)

(73) Assignee: Innophore GmbH, Graz (AT)

( * ) Notice: Subject to any disclaimer, the term of this patent is extended or adjusted under 35 U.S.C. 154(b) by 0 days.

(21) Appl. No.: 14/647,063

(22) PCT Filed: Nov. 25, 2013

(86) PCT No.: PCT/EP2013/074556
§ 371 (c)(1),
(2) Date: May 22, 2015

(87) PCT Pub. No.: WO2014/080005
PCT Pub. Date: May 30, 2014

(65) Prior Publication Data
US 2015/0302142 A1 Oct. 22, 2015

(30) Foreign Application Priority Data
Nov. 26, 2012 (EP) ..................................... 12194206

(51) Int. Cl.
*G16B 15/00* (2019.01)
*G16B 35/00* (2019.01)
*G16B 50/00* (2019.01)
*G16C 20/60* (2019.01)

(52) U.S. Cl.
CPC ............ *G16B 15/00* (2019.02); *G16B 35/00* (2019.02); *G16B 50/00* (2019.02); *G16C 20/60* (2019.02)

(58) Field of Classification Search
CPC combination set(s) only.
See application file for complete search history.

(56) References Cited

U.S. PATENT DOCUMENTS

| 2003/0130179 A1* | 7/2003 | Shepard ............ A61K 47/48138 702/19 |
| 2006/0257387 A1* | 11/2006 | Nakayama ............ C12N 9/1051 424/94.61 |
| 2012/0100594 A1* | 4/2012 | Baker ...................... C12N 9/16 435/193 |

FOREIGN PATENT DOCUMENTS

WO    00/23474    4/2000

OTHER PUBLICATIONS

Halligan et al. Journal of Proteome Research 2009, 8, 3148-3153 (Year: 2009).*
Lindstrom et al. The Scripps Research Institute Molecular Graphics Laboratory, La Jolla, California, USA Jan. 29, 2008, v2, 1-37.*
Fober et a., (2011) IEEE/ACM Transactions on Computational Biology and Bioinformatics, vol. 8 (6), art. No. 5722954, pp. 1653-1666; "Superposition and Alignment of Labeled Point Clouds", 6, Feb. 24, 2011, pp. 1653-1666.
Fober Thomas et al. "Efficient Construction of Multiple Geometrical Alignments for the Comparison of Protein Binding Sites", 2009, ISDA 2009—9th International Conference on Intelligent Systems Design and Applications, art. No. 5364137, pp. 1251-1256.
Gruber K et al..: "The catalophore concept: Identification of catalytic promiscuity by mining of structural databases", Proceedings of the 6th International Congress on Biocatalysis—BIOCAT 2012, Sep. 2-6, 2012, Hamburg, Germany, Sep. 2, 2012 (Sep. 2, 2012),-Sep. 6, 2012 (Sep. 6, 2012).
Leinweber et al., (2012) IEEE International Conference on Digital Ecosystems and Technologies, art. No. 6227926; "GPU-based cloud computing for comparing the structure of protein binding sites", pp. 1-6.
Steinkellner G., et al: "Catalophore: Mining of structural databases using 3D-templates", BIOTRANS 2011, Giardini Naxos, Sicily, Italy, Oct. 2-6, 2011, Oct. 2, 2011 (Oct. 2, 2011),-Oct. 6, 2011 (Oct. 6, 2011).
International Search Report & Written Opinion for PCT/EP13/74556 dated Mar. 3, 2014; 14 pages.
International Preliminary Report on Patentability for PCT/EP13/74556 dated May 26, 2015; 9 pages.
European Search Report for EP Serial No. 12194206.4 dated Apr. 15, 2015; 11 pages.
Schmitt et al., "A New Method to Detect Related Function Among Proteins Independent of Sequence and Fold Homology," *J. Mol. Biol.* 323:387-406, 2002.

* cited by examiner

*Primary Examiner* — Michael L Borin
(74) *Attorney, Agent, or Firm* — Seed IP Law Group LLP

(57) ABSTRACT

The invention relates to a method for determining catalophores including the steps of creating a point cloud database for target protein structures; creating a query point cloud; and searching said database with said query to thereby identify one or more catalophores.

21 Claims, 3 Drawing Sheets

DETERMINING NOVEL ENZYMATIC FUNCTIONALITIES USING THREE-DIMENSIONAL POINT CLOUDS REPRESENTING PHYSICO CHEMICAL PROPERTIES OF PROTEIN CAVITIES

CROSS-REFERENCE TO RELATED APPLICATIONS

This application is the U.S. national stage of International Patent Application No. PCT/EP2013/074556, filed on Nov. 25, 2013 and entitled DETERMINING NOVEL ENZYMATIC FUNCTIONALITIES USING THREE-DIMENSIONAL POINT CLOUDS REPRESENTING PHYSICO CHEMICAL PROPERTIES OF PROTEIN CAVITIES, which claims the benefit of priority under 35 U.S.C. § 119 from European Patent Application No. 12194206.4, filed Nov. 26, 2012. The disclosures of the foregoing applications are incorporated herein by reference in their entirety.

The invention relates to a method for designing catalophores including the steps of creating a point cloud database for target protein structures; creating a query point cloud; and searching said database with said query to thereby identify one or more catalophore.

BACKGROUND

Enzymes are increasingly utilized in biotechnological and biocatalytic processes. Despite numerous successful applications, however, it became clear that not all potentially interesting chemical reactions are represented in the current enzyme portfolio. In addition, natural enzymes are generally not fully optimized for their utilization in industrial processes. Thus the identification and/or design of novel enzyme functionalities and the improvement of existing enzymes are of outmost importance.

Several approaches for identifying protein binding sites have been described in literature. For example, a GPU-based cloud computing infrastructure has been used to efficiently perform a structural comparison of protein binding sites (Leinweber et al., (2012) IEEE International Conference on Digital Ecosystems and Technologies, art. no. 6227926).

A labelled point cloud model has been described to be suitable for modelling biomolecules such as proteins and protein binding sites, where a label may represent an atom type or a physico-chemical property (Fober et a., (2011) IEEE/ACM Transactions on Computational Biology and Bioinformatics, 8 (6), art. no. 5722954, pp. 1653-1666).

A method for protein structure comparison in which information about the geometry and physico-chemical properties of such structures are represented in the form of labeled point clouds has been described by Fober et al. ((2009) ISDA 2009-9th International Conference on Intelligent Systems Design and Applications, art. no. 5364137, pp. 1251-1256).

WO0023474 discloses a method of protein engineering wherein a searchable computer database is created comprising entries in the form of descriptions of a location and orientation in 3D space of side chains of the constituent amino acid residues of a framework protein for identifying a hit which corresponds to a framework protein having structural similarity with a sample protein.

SHORT DESCRIPTION OF THE INVENTION

The invention relates to protein engineering and design efforts based on an integration of structural and mechanistic studies and directed evolution approaches to achieve an optimal and efficient strategy determining novel enzymatic functionalities using three-dimensional point clouds representing physico chemical properties of protein cavities.

Apart from their original catalytic activity, some enzymes have been shown to also catalyse completely different chemical reactions as a side activity. This so called "catalytic promiscuity" can be the starting point to design a proficient enzyme catalysing a non-natural chemical reaction. The catalytic promiscuity in enzymes is the ability of enzymes to catalyse distinctly different chemical transformations. The chemical transformation may differ in the functional group involved, that is, the type of bond formed or cleaved during the reaction and/or may differ in the catalytic mechanism or path of bond making and breaking. So far, however, the identification of catalytic promiscuity was based on serendipity. The screening of structural databases with functional motifs "catalophores", which are based on physico-chemical properties, represents a more rational approach to predict "catalytic promiscuity" in enzymes. Using this state-of-the-art method we have recently been successful in identifying two enzymes which are predicted to exhibit interesting enoate-reductase activities but do not show any similarity (on the sequence as well as on the structural level) to known enoate-reductases (old yellow enzymes). In this case, the design of the functional motifs used for database screening relied on a large amount of structural and mechanistic information available for this enzyme class. However, this approach could also involve a theoretical active site structural motif derived from the mechanistic requirements of a particular chemical reaction.

In addition to exploiting catalytic promiscuity in existing natural enzymes novel enzyme functionalities can be created through the de-novo design of active sites by grafting catalytically important residues onto stable protein scaffolds. Obviously, this approach also requires detailed mechanistic knowledge and can greatly benefit from the huge amount of data on non-enzymic organo- and organo-metallic catalysts used in solution chemistry. Examples in the literature indicate that the proof-of-principle for such an approach has been achieved. As yet, however, it has not been used to design a novel catalyst for industrial biocatalysis.

Very often the catalytic activity of an enzyme is achieved by a small domain of a larger protein which might include other domains necessary for the physiological function but irrelevant for the biotechnological application. The reduction of the size of the catalyst—i.e. the design of a "minimal enzyme"—potentially has huge benefits for the expression of the protein, the process stability or for the engineering by directed evolution.

DETAILED DESCRIPTION OF THE INVENTION

Therefore a method to find catalophores with specific active site geometries by using a three-dimensional distance template mimicking a minimal catalytic active site constellation was developed.

In the context of this invention the term "catalophore" refers to the description of the active site of a protein, preferably of an enzyme. A catalophore also encompasses a minimal enzyme or part or fragment of an enzyme that comprises the active site of said enzyme including the 3D descriptors of the active site.

According to the invention the active site may be, but is not restricted to, an enzymatic, catalytic, receptor binding or protein expression regulating site.

Specifically in case the catalophore identified by the inventive method, is an isolated catalophore domain, said catalophore domain preferably has the same or similar characteristics/activity as the catalophore domain present in the parent protein. Alternatively said catalophore domain may by modified to have increased enzymatic, catalytic activity compared to the parent domain.

Accordingly, in a first aspect the invention provides a method for determining a catalophore of a protein including the steps of a) creating a point cloud database for target protein structures;
b) creating a query point cloud;
c) searching said database with said query to thereby identify one or more catalophores.

A further aspect of the invention is the method as described above, wherein one point cloud is calculated for each physico-chemical property of the target proteins.

A further aspect of the invention is the method as described above, wherein point clouds for additional interactions as H-bonds for target protein structures are calculated.

A further aspect of the invention is the method as described above, wherein the query point cloud is a set of point clouds.

A further aspect of the invention is the method as described above, wherein said set of point clouds is derived from the catalytic activity of target proteins or from the quantum mechanical models of template reactions.

A further aspect of the invention is the method as described above, wherein said query point clouds and said point cloud database are superimposed.

A further aspect of the invention is the method as described above, wherein said query point cloud is rotated and translated by random.

A further aspect of the invention is the method as described above, wherein said target protein structures are homogenized.

A further aspect of the invention is an enzyme comprising a catalophore, wherein said catalophore is obtained by a method as described above.

A further aspect of the invention is a method of constructing a pool of catalophores with pre-defined catalytic and physico-chemical properties, wherein said catalophore is obtained by a method as described above.

A further aspect of the invention is a pool of catalophores with pre-defined properties obtained by a method as described above.

A further aspect of the invention is the use of a catalophore as catalyst for industrial biocatalysis.

Possible hits in structural databases were experimentally tested for the desired activity and improved properties for industrial application. As an example the search template was derived from the active site of old yellow enzymes (OYE). Members of the well-known enoate-reductase family have been shown to possess a high potential as biocatalysts in asymmetric reduction of activated alkenes. Proteins from the OYE family catalyse the reduction of activated C═C bonds in α,β-unsaturated compounds, and it has been shown that they represent an efficient, biocatalytic alternative to standard organic synthesis. Besides, in the flavin mononucleotide (FMN) cofactor the catalytic site itself usually comprises a pair of residues (typically histidine/histidine or asparagine/histidine) that act as H-bonding donors to the electron-withdrawing group of the substrate and a conserved tyrosine residue, which is necessary to deliver a proton onto the C atom during turnover.

It is an object of the invention to spot other enzymes with enoate-reductase functionality in structural databases even within this intensively investigated family. Therefore a relatively simple three dimensional active site image was used, generated by comparison of active site features of representative OYE structures to search for other enzymes with this specific active site constellation. As a search platform the commercially available Relibase+ database (v. 2.2) was used, which contains pre-processed structural information. In addition an in-house database (CATALObase) was developed of pre-processed structures that were prepared by applying YASARA structure functions. For the Relibase+ search the active site image was created using the Relibase+ 2D/3D builder. The 3D active site image for the search using the in-house database was generated using a YASARA script. With both search approaches typical OYE structures as well as two "novel" proteins with predicted old yellow enzyme activities were identified. The pocket database CavBase was also used which is embedded in the Relibase+ database and which contains information about active site cavities and abstracted pseudo centres. In the case of the OYE's and using the settings as described before, the proteins that were found with the pure geometric approach within the first 200 CavBase hits could not be identified.

The final catalophore search resulted in a manageable amount of 46 hits that could be further reduced by applying a filter to winnow the obvious hits of known OYEs. This was done by sequence (using BLAST) and structural comparison using PDBefold as well as by OYE sequence pattern classification, leaving only the novel enzymes with a similar active site arrangement. Thus narrowed results revealed several structures consisting of the active site constellation requirements of the template to 6 hits.

By visual inspection two oxidoreductases (PDB Code: 2i0k and 3fbs) were identified where the tyrosine residue has the required distance but is on the opposite side of the flavin cofactor and the active site cavity, thus unable to provide the proton for a potential substrate. The also identified flavoprotein subunit of a mutated (N204Y) furmarate reductase was discarded in the first round of investigation, because of the heme hetero component which may have disturbed proper old yellow enzyme analytics. The putative monooxygenase (PDB Code: 1usc and 1usf) and the uncharacterized protein PH0856 (PDB Code: 2r6v) were thus selected for investigation and characterization. The found enzymes are neither sequentially nor, and this is a more surprising result, structurally related to any known OYE structures. The active site constellation showed approximate a mirror-image symmetry to the template structures, suggesting a different stereo chemical outcome. The putative monooxygenase from *Thermus thermophilus* and the uncharacterized protein PH0856 from *Pyrococcus horikoshii* are in the following text referred to Tth and Pho, respectively, based the organisms where they were isolated. The biocatalytic activity of these enzymes has been experimentally evaluated. In conclusion two enzymes have successfully been identified with as yet unknown function which were found to have a similar active site architecture compared to classical enoate-reductases and do not show any similarity neither on sequence nor on a global structural level to any known OYEs.

As a further embodiment said domain can be introduced into protein scaffolds, wherein the secondary/tertiary structure of the catalophore is preserved in order to keep its functionality. As an alternative embodiment, the catalophore may be modified by techniques known to the skilled person, for example by random mutagenesis to improve or change its functionality, specifically in view of enzymatic, target binding or catalytic activity.

SHORT DESCRIPTION OF THE FIGURES

EXAMPLES

Example 1—Generation of Point Clouds

This approach for identifying catalytic active motifs "catalophores" is based on the implementation of new protocols repurposing pre-calculated grid maps of target protein structures generated with a modified version of AutoGrid4 that is part of the AutoDock4 software suite. One point cloud is calculated for each physico-chemical property type as well as special purpose point clouds representing additional interactions as H-bonds (Table 1 and FIG. 1).

TABLE 1

| Physico-chemical properties | | | |
|---|---|---|---|
| Entry | Type | | Examples |
| 1 | potential energies | non H-bonding atoms | sulphur, chlorine, calcium, manganese, iron, zinc, bromine, iodine, fluorine, magnesium, phosphorus, aliphatic carbon, aromatic carbon, nitrogen, hydrogen |
| | | H-bond acceptors | nitrogen, sulphur, oxygen |
| | | H-bond donors | hydrogen |
| 2 | electrostatic potential | | |
| 3 | hydrophobicity | | |
| 4 | accessibility | | |

Figure 1:
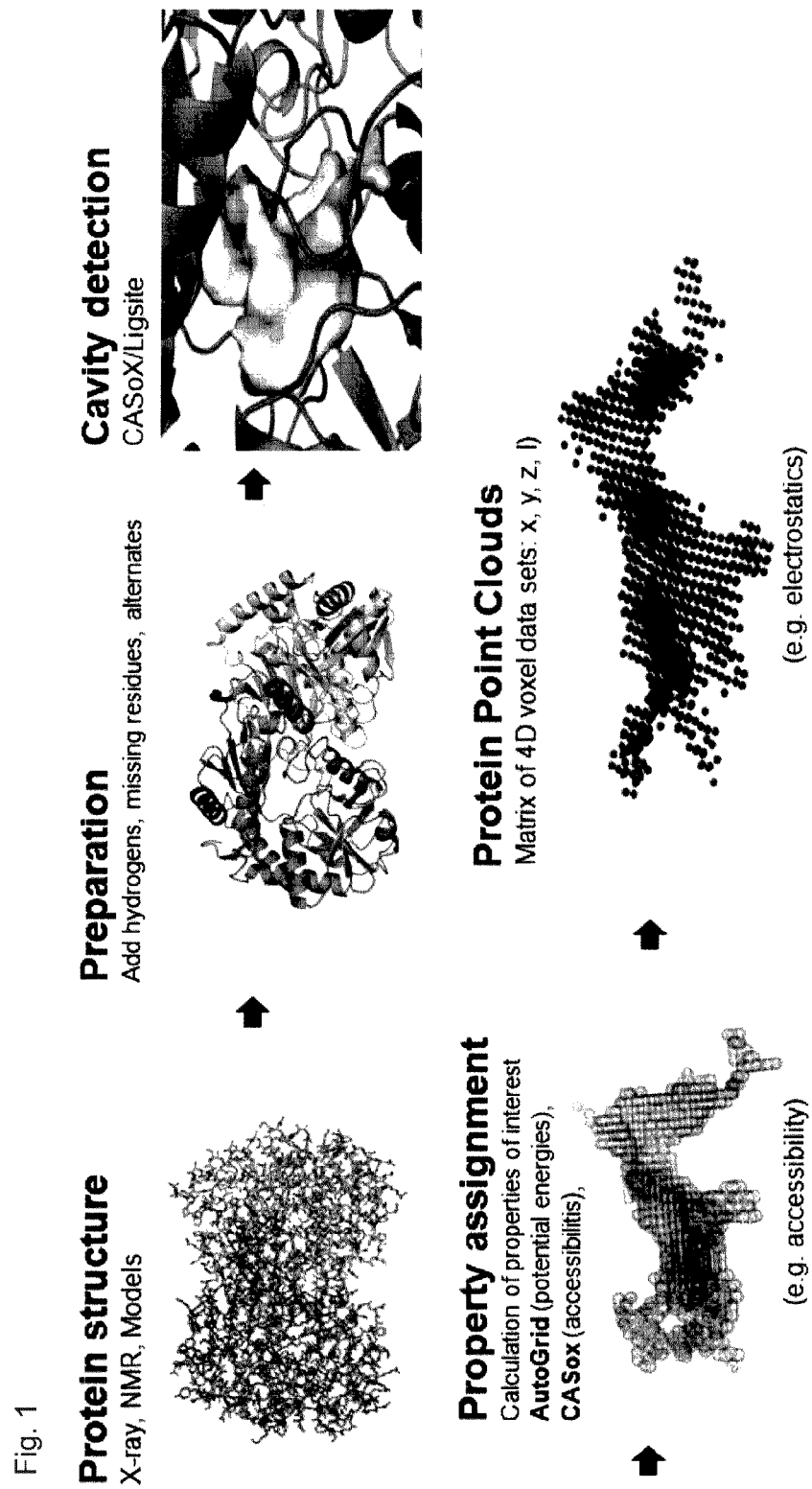
FIG. 1 depicts the preparation of protein point clouds.

These target grid maps are converted to point cloud data files to be further processed within the catalophore software pipeline. Protein structures are prepared following standard protocols for the addition of hydrogen atoms, addition of missing atoms and residues followed by automatic cavity detection (FIG. 1). Areas identified as protein cavities suitable for the binding of potential substrates are subsequently characterized and stored as property point clouds.

Figure 2:
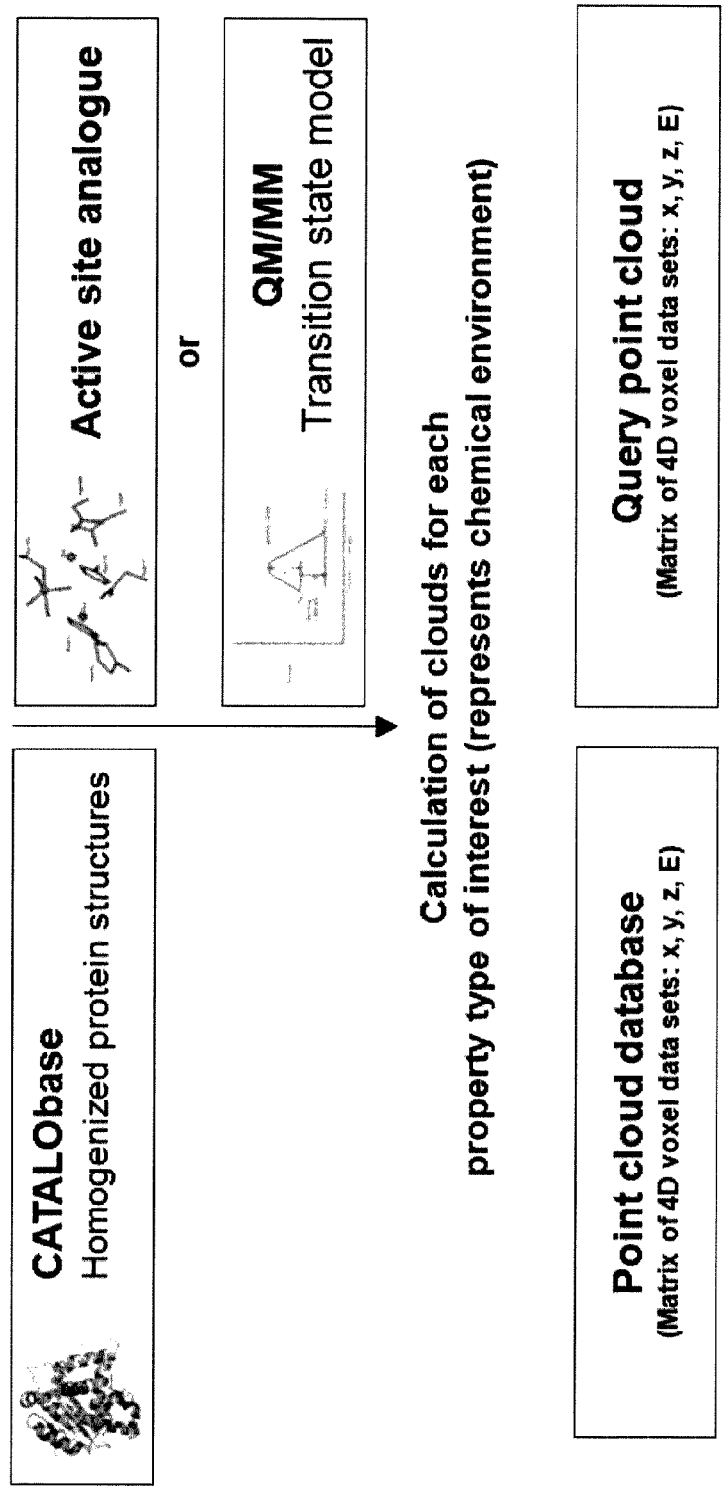
FIG. 2 depicts the workflow of the point cloud matching process.

One set of point clouds is required to describe the "search query". These point clouds can be derived from enzymes featuring the desired catalytic activity or from quantum mechanical models of template reactions. These point clouds are compared to point clouds that were previously calculated for all available protein structures (FIG. 2).

Example 2—Establishing a Catalophore Database

In order to homogenize target protein structures and create point clouds for each identified cavity, structures from various sources "fridges" are collected and stored in a standardized format in a relational database system CATALObase (Table 2).

TABLE 2

| Data sources | | |
|---|---|---|
| Entry | Fridge | Update interval |
| 1 | RCSB PDB | daily |
| 2 | PDBe PISA | daily |
| 3 | Homology models | continuously |
| 4 | In house structures | as requested |
| 5 | Mutants and variants | as requested |

For each of these protein structures point clouds are automatically generated and stored for the following matching process.

Example 3—Matching of Query Catalophores with Database Entries

Figure 3:
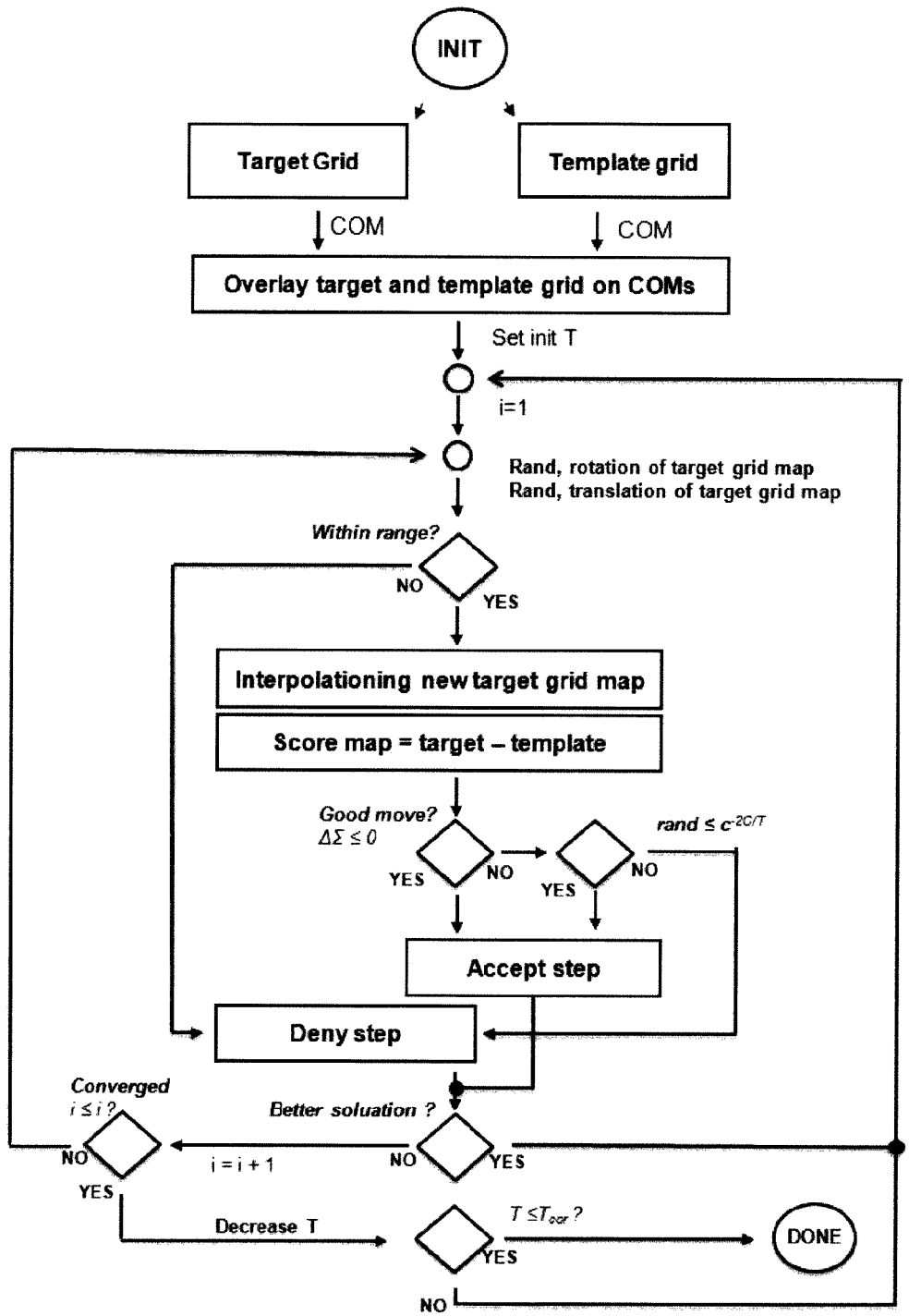
FIG. 3 depicts the matching process.

The query and the database point clouds are superimposed and the deviation of the two grid maps is evaluated by comparing the closest grid points between the target and the template. For each point cloud type one "identity score" is generated representing the quality of the match. This individual score (Equation 1) is weighted by a selectable factor to allow fine-tuning the influence of the different grid maps (for instance setting the scoring factor for the H-bond point clouds to zero causes this interaction to be ignored). After evaluating the quality of the match, the query point cloud is rotated and translated by random. If the obtained new complex is better than the previous, this step is accepted. The procedure is repeated until no better match can be obtained (FIG. 3). The algorithms were implemented in a standalone version of the CATALOphore software in C++ based on the freely available source code of AutoDock4 and the PCL (The Point Cloud Library (PCL)).

CATALOphore identity score $$\text{score} = \sum_i \text{score}_{point} \quad \text{Equation 1}$$

$$\text{score}_{point} = \sum_{type=A,C,d,e,HD,N,NA,OA,SA,\ldots} \text{score}_{type}$$

$$\text{score}_{point}^{type} = |E_{query} - E_{target}|$$

Example 4

To test the above-described procedure we extracted point clouds for enzymes belonging to the group of old yellow enzymes. These query point clouds were compared to a test subset of the CATALObase containing point clouds representing 10 diverse protein structures (old yellow enzymes, alcohol dehydrogenases and lipases). Table 2 summarizes the results of the matching process. The best match was obtained for the protein structure used for the query design, as expected. Ranked by our "identity score" the following two hits are enzymes that have been previously shown to have old-yellow-enzyme like activity but were not annotated nor biochemically characterized. A negative and positive control was ranked as expected.

TABLE 2

Top 5 results of the old-yellow-enzyme example

| Entry | Protein | PDB code | Identity score | Comments |
|---|---|---|---|---|
| 1 | Old yellow enzyme | 1OYA | 97% | used for query point cloud creation |
| 2 | Old yellow enzyme | 2GQ9 | 84% | structurally similar to 1OYA, positive control |
| 3 | Putative styrene monooxygenase | 1USC | 83% | experimentally observed OYE activity |
| 4 | Uncharacterized protein PH0856 | 2R6V | 81% | experimentally observed OYE activity |
| 5 | Lipase | 1TCA | 14% | negative control |

The invention claimed is:

1. A method of screening for a catalyst of a predetermined chemical reaction, comprising:
   a) determining physico-chemical properties within an active site cavity of a first enzyme, wherein the physico-chemical properties comprise at least two physico-chemical properties selected from: a potential energy, an electrostatic potential, a hydrophobicity, and an accessibility, and wherein the active site cavity is suitable for the binding of a substrate and catalyzes the predetermined chemical reaction;
   b) calculating a three-dimensional point cloud for each determined physico-chemical property within the active site cavity of the first enzyme, thereby creating a query point cloud; and
   c) searching a database comprising corresponding point clouds for active site cavities of predetermined proteins by comparing the corresponding point clouds with the query point cloud to thereby identify a predetermined protein which has a cavity corresponding to the active site cavity of the first enzyme, thereby identifying a second enzyme,
      wherein the comparing comprises superimposing the query point cloud and a corresponding point cloud from the database and randomly rotating and translating the query point cloud.

2. The method of claim 1, wherein one point cloud is calculated for each physico-chemical property of the predetermined proteins.

3. The method of claim 1, wherein the query point cloud comprises a set of point clouds.

4. The method of claim 3, wherein the set of point clouds is derived from catalytic activity of predetermined proteins or from quantum mechanical models of template reactions.

5. The method of claim 1, wherein the active site cavities of predetermined proteins of the database in c) are homogenized.

6. The method of claim 1, wherein a plurality of catalysts of the predetermined chemical reaction are identified, thereby constructing a pool of enzyme catalysts.

7. The method of claim 1, further comprising, prior to c), creating the database comprising corresponding point clouds for active site cavities of predetermined proteins that is searched in c).

8. The method of claim 1, wherein:
   (i) the calculating a point cloud in b) comprises using a target grid map comprising target grid points of the active site cavity of the first enzyme;
   (ii) the corresponding point clouds in c) were calculated using template grid maps comprising template grid points of the active site cavities of the predetermined proteins; and
   (iii) the comparing in c) comprises comparing the target grid points and the template grid points, thereby determining a deviation between the one or more query point clouds and a corresponding point cloud.

9. The method of claim 1, wherein the searching in c) further comprises generating an identity score for each point cloud type.

10. The method of claim 1, wherein the at least two physico-chemical properties are selected from:
    (i) potential energy of a non H-bonding atom, wherein the non-H-bonding atom comprises one or more of: sulphur, chlorine, calcium, manganese, iron, zinc, bromine, iodine, fluorine, magnesium, phosphorus, aliphatic carbon, aromatic carbon, nitrogen, and hydrogen;
    (ii) potential energy of an H-bond acceptor, wherein the H-bond acceptor comprises one or more of: nitrogen, Sulphur, and oxygen;
    (iii) potential energy of an H-bond donor, wherein the H-bond donor comprises hydrogen;
    (iv) electrostatic potential;
    (v) hydrophobicity; and
    (vi) accessibility.

11. The method of claim 9, wherein the identity score is generated using Equation 1.

12. The method of claim 1, further comprising d) producing the second enzyme, thereby providing the catalyst of the predetermined chemical reaction.

13. The method of claim 12, further comprising e) testing the second enzyme for catalysis of the predetermined chemical reaction.

14. The method of claim 13, wherein the second enzyme exhibits increased catalytic activity of the predetermined chemical reaction as compared to the first enzyme.

15. A method of screening for a protein with a binding site suitable for a predetermined chemical reaction, comprising:
    a) determining physico-chemical properties within a cavity of a first protein, wherein the physico-chemical properties comprise at least two: of a potential energy, an electrostatic potential, an accessibility, or a hydrophobicity, and wherein the cavity is suitable for the binding of a substrate of a predetermined chemical reaction;
    b) calculating a three-dimensional point cloud for each determined physico-chemical property within the cavity of the first protein, thereby creating a query point cloud; and
    c) searching a database comprising corresponding point clouds for cavities of predetermined proteins by comparing the corresponding point clouds with the query point cloud to thereby identify a predetermined protein which has an active site cavity corresponding to the cavity of the first protein, thereby identifying a second protein, wherein the comparing comprises superimposing the query point cloud and the corresponding point clouds from the database and randomly rotating and translating the query point cloud.

16. The method of claim 15, wherein one point cloud is calculated for each physico-chemical property of the predetermined proteins.

17. The method of claim 15, wherein:
(i) the calculating a point cloud in b) comprises using a target grid map comprising target grid points of the cavity of the first protein;
(ii) the corresponding point clouds in c) were calculated using template grid maps comprising template grid points of the cavities of the predetermined proteins; and
(iii) the comparing in c) comprises comparing the target grid points and the template grid points, thereby determining a deviation between the query point cloud and a corresponding point cloud.

18. The method of claim 15, wherein the one or more physico-chemical properties is selected from the group consisting of: potential energies, electrostatic potential, hydrophobicity, accessibility, or any combination thereof.

19. A method of screening for a catalyst of a predetermined chemical reaction, comprising:
determining physico-chemical properties at the location of grid voxels, wherein the grid includes a cavity of a first enzyme, wherein the physico-chemical properties comprise at least two physico-chemical properties selected from: a potential energy, an electrostatic potential, a hydrophobicity, an accessibility, and wherein the cavity is suitable for binding of a substrate and catalyzes the predetermined chemical reaction;
calculating a point cloud for each determined physico-chemical property of the cavity of the first enzyme, thereby creating a query point cloud; and
searching a database comprising corresponding point clouds for active site cavities of predetermined proteins by comparing the corresponding point clouds with the query point cloud to thereby identify a predetermined protein which has an active site cavity corresponding to the cavity of the first enzyme, thereby identifying a second enzyme, wherein the comparing comprises comparing the physico-chemical properties at grid voxels of the query point cloud to the phyico-chemical properties at the closest grid voxels of the corresponding point clouds from the point cloud database, wherein the comparing comprises superimposing the query point cloud and a corresponding point cloud from the database and randomly rotating and translating the query point cloud, and generating an identity score as a weighted sum of the individual identity scores.

20. The method of claim 18, wherein the physico-chemical properties comprise at least three physico-chemical properties selected from: a potential energy, an electrostatic potential, a hydrophobicity, an accessibility.

21. The method of claim 1, wherein the physico-chemical properties comprise at least three physico-chemical properties selected from: a potential energy, an electrostatic potential, a hydrophobicity, an accessibility.

* * * * *